United States Patent
Estell

(10) Patent No.: US 6,316,241 B1
(45) Date of Patent: Nov. 13, 2001

(54) ALPHA/BETA HYDROLASE-FOLD ENZYMES

(75) Inventor: David A. Estell, San Mateo, CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 09/355,166

(22) PCT Filed: Nov. 19, 1998

(86) PCT No.: PCT/US98/24973

§ 371 Date: Sep. 27, 1999

§ 102(e) Date: Sep. 27, 1999

(87) PCT Pub. No.: WO99/27081

PCT Pub. Date: Jun. 3, 1999

(30) Foreign Application Priority Data

Nov. 20, 1997 (GB) ................................... 9724629

(51) Int. Cl.⁷ ....................................................... C12N 9/50
(52) U.S. Cl. .................... 435/219; 435/222; 435/252.31; 435/320; 435/212; 510/392; 8/401
(58) Field of Search ................................. 435/183, 252.3, 435/195, 212, 222, 219, 252.31, 220, 221, 320.1; 536/23.1, 23.2; 510/392; 8/401

(56) References Cited

U.S. PATENT DOCUMENTS

| | | | | |
|---|---|---|---|---|
| 4,533,359 | * | 8/1985 | Kondo et al. ............................ | 8/128 |
| 5,204,015 | * | 4/1993 | Caldwell et al. ................ | 252/174.12 |
| 5,612,055 | * | 3/1997 | Bedford et al. ....................... | 424/442 |

OTHER PUBLICATIONS

Jung et al. Expression of the colH gene encoding *Clostridium histolyticum* collagenase in *Bacillus subtilis* and its application to enzyme purification. Microbiol Immunol. 1996, vol. 40, pp. 923–929, 1996.*
Kawamura et al. Construction of a *Bacillus subtilis* double mutant deficient in extracellularalkaline and neutral proteases. J Bacteriol. Oct. 1984, vol. 160, pp. 442–444, Oct. 1984.*
Zhang et al. Cloning, sequencing and regulation of thiA, a thiamin biosynthesis gene from*Bacillus subtilis*. Gene. Oct. 1, 1997, vol. 198, pp. 73–82.*
Bower et al. Accession No. U51868, Oct. 25, 1996.*
Denizot. Accession No. Z94043, Apr. 28, 1997.*
Carrer et al. Accession No. Q40706, Aug. 17, 1993.*
Roels et al. Accession No. AF015775, Oct. 4, 1997.*
Kunst et al. Accession No. P39839; 032120, Feb. 1, 1995.*
Levine et al. Accession No. P70948; 008141, Feb. 1, 1997.*
Kobayashi et al. Accession No. P54567, Oct. 1, 1996.*
Yamane et al. Accession No. P94407, May 1, 1997.*
Kasahara et al. Accession No. P96671, May 1, 1997.*
Kunst et al. Accession No. 007015, Jul. 1, 1997.*
Koybayashi et al. Accession No. P54549, Oct. 1, 1996.*
Rodriguez. Accession No. R34715, Aug. 17, 1993.*
Kunst et al. Accession No. P94396, May 1, 1997.*
Yasumoto et al. Accession No. P70981, Feb. 1, 1997.*

* cited by examiner

Primary Examiner—Nashaat T. Nashed
Assistant Examiner—Christian L. Fronda
(74) Attorney, Agent, or Firm—Genencor Intl. Inc.

(57) ABSTRACT

The present invention relates to the identification of novel hydrolases in gram positive microorganisms. The present invention provides amino acid sequences for the hydrolase. The present invention provides host cells which comprise nucleic acid encoding the hydrolase. The present invention also provides cleaning compositions, animal feeds and compositions used to treat a textile that include the hydrolase of the present invention.

21 Claims, No Drawings

SEQUENCE LISTING

<160> NUMBER OF SEQ ID NOS: 21

<210> SEQ ID NO 1
<211> LENGTH: 657
<212> TYPE: PRT
<213> ORGANISM: Bacillus

<400> SEQUENCE: 1

Met Lys Lys Leu Ile Thr Ala Asp Asp Ile Thr Ala Ile Val Ser Val
 1               5                   10                  15

-continued

```
Thr Asp Pro Gln Tyr Ala Pro Asp Gly Thr Arg Ala Ala Tyr Val Lys
            20                  25                  30

Ser Gln Val Asn Gln Glu Lys Asp Ser Tyr Thr Ser Asn Ile Trp Ile
        35                  40                  45

Tyr Glu Thr Lys Thr Gly Gly Ser Val Pro Trp Thr His Gly Glu Lys
    50                  55                  60

Arg Ser Thr Asp Pro Arg Trp Ser Pro Asp Gly Arg Thr Leu Ala Phe
65                  70                  75                  80

Ile Ser Asp Arg Glu Gly Asp Ala Ala Gln Leu Tyr Ile Met Ser Thr
                85                  90                  95

Glu Gly Gly Glu Ala Arg Lys Leu Thr Asp Ile Pro Tyr Gly Val Ser
            100                 105                 110

Lys Pro Leu Trp Ser Pro Asp Gly Glu Ser Ile Leu Val Thr Ile Ser
        115                 120                 125

Leu Gly Glu Gly Glu Ser Ile Asp Asp Arg Glu Lys Thr Glu Gln Asp
    130                 135                 140

Ser Tyr Glu Pro Val Glu Val Gln Gly Leu Ser Tyr Lys Arg Asp Gly
145                 150                 155                 160

Lys Gly Leu Thr Arg Gly Ala Tyr Ala Gln Leu Val Leu Val Ser Val
                165                 170                 175

Lys Ser Gly Glu Met Lys Glu Leu Thr Ser His Lys Ala Asp His Gly
            180                 185                 190

Asp Pro Ala Phe Ser Pro Asp Gly Lys Trp Leu Val Phe Ser Ala Asn
        195                 200                 205

Leu Thr Glu Thr Asp Asp Ala Ser Lys Pro His Asp Val Tyr Ile Met
    210                 215                 220

Ser Leu Glu Ser Gly Asp Leu Lys Gln Val Thr Pro His Arg Gly Ser
225                 230                 235                 240

Phe Gly Ser Ser Phe Ser Pro Asp Gly Arg Tyr Leu Ala Leu Leu
                245                 250                 255

Gly Asn Glu Lys Glu Tyr Lys Asn Ala Thr Leu Ser Lys Ala Trp Leu
            260                 265                 270

Tyr Asp Ile Glu Gln Gly Arg Leu Thr Cys Leu Thr Glu Met Leu Asp
        275                 280                 285

Val His Leu Ala Asp Ala Leu Ile Gly Asp Ser Leu Ile Gly Gly Ala
    290                 295                 300

Glu Gln Arg Pro Ile Trp Thr Lys Asp Ser Gln Gly Phe Tyr Val Ile
305                 310                 315                 320

Gly Thr Asp Gln Gly Ser Thr Gly Ile Tyr Tyr Ile Ser Ile Glu Gly
                325                 330                 335

Leu Val Tyr Pro Ile Arg Leu Glu Lys Glu Tyr Ile Asn Ser Phe Ser
            340                 345                 350

Leu Ser Pro Asp Glu Gln His Phe Ile Ala Ser Val Thr Lys Pro Asp
        355                 360                 365

Arg Pro Ser Glu Leu Tyr Ser Ile Pro Leu Gly Gln Glu Glu Lys Gln
    370                 375                 380

Leu Thr Gly Ala Asn Asp Lys Phe Val Arg Glu His Thr Ile Ser Ile
385                 390                 395                 400

Pro Glu Glu Ile Gln Tyr Ala Thr Glu Asp Gly Val Met Val Asn Gly
                405                 410                 415

Trp Leu Met Arg Pro Ala Gln Met Glu Gly Glu Thr Thr Tyr Pro Leu
            420                 425                 430

Ile Leu Asn Ile His Gly Gly Pro His Met Met Tyr Gly His Thr Tyr
```

-continued

```
                435                 440                 445
Phe His Glu Phe Gln Val Leu Ala Ala Lys Gly Tyr Ala Val Val Tyr
    450                 455                 460

Ile Asn Pro Arg Gly Ser His Gly Tyr Gly Gln Glu Phe Val Asn Ala
465                 470                 475                 480

Val Arg Gly Asp Tyr Gly Gly Lys Asp Tyr Asp Val Met Gln Ala
                485                 490                 495

Val Asp Glu Ala Ile Lys Arg Asp Pro His Ile Asp Pro Lys Arg Leu
            500                 505                 510

Gly Val Thr Gly Gly Ser Tyr Gly Gly Phe Met Thr Asn Trp Ile Val
            515                 520                 525

Gly Gln Thr Asn Arg Phe Lys Ala Ala Val Thr Gln Arg Ser Ile Ser
        530                 535                 540

Asn Trp Ile Ser Phe His Gly Val Ser Asp Ile Gly Tyr Phe Phe Thr
545                 550                 555                 560

Asp Trp Gln Leu Glu His Asp Met Phe Glu Asp Thr Glu Lys Leu Trp
                565                 570                 575

Asp Arg Ser Pro Leu Lys Tyr Ala Ala Asn Val Glu Thr Pro Leu Leu
            580                 585                 590

Ile Leu His Gly Glu Arg Asp Asp Arg Cys Pro Ile Glu Gln Ala Glu
            595                 600                 605

Gln Leu Phe Ile Ala Leu Lys Lys Met Gly Lys Glu Thr Lys Leu Val
        610                 615                 620

Arg Phe Pro Asn Ala Ser His Asn Leu Ser Arg Thr Gly His Pro Arg
625                 630                 635                 640

Gln Arg Ile Lys Arg Leu Asn Tyr Ile Ser Ser Trp Phe Asp Gln His
                645                 650                 655

Leu

<210> SEQ ID NO 2
<211> LENGTH: 256
<212> TYPE: PRT
<213> ORGANISM: Bacillus

<400> SEQUENCE: 2

Met Ile Val Glu Lys Arg Arg Phe Pro Ser Pro Ser Gln His Val Arg
1               5                   10                  15

Leu Tyr Thr Ile Cys Tyr Leu Ser Asn Gly Leu Arg Val Lys Gly Leu
            20                  25                  30

Leu Ala Glu Pro Ala Glu Pro Gly Gln Tyr Asp Gly Phe Leu Tyr Leu
        35                  40                  45

Arg Gly Gly Ile Lys Ser Val Gly Met Val Arg Pro Gly Arg Ile Ile
50                  55                  60

Gln Phe Ala Ser Gln Gly Phe Val Val Phe Ala Pro Phe Tyr Arg Gly
65              70                  75                  80

Asn Gln Gly Gly Glu Gly Asn Glu Asp Phe Ala Gly Glu Asp Arg Glu
                85                  90                  95

Asp Ala Phe Ser Ala Phe Arg Leu Leu Gln Gln His Pro Asn Val Lys
            100                 105                 110

Lys Asp Arg Ile His Ile Phe Gly Phe Ser Arg Gly Gly Ile Met Gly
        115                 120                 125

Met Leu Thr Ala Ile Glu Met Gly Gly Gln Ala Ala Ser Phe Val Ser
130                 135                 140

Trp Gly Gly Val Ser Asp Met Ile Leu Thr Tyr Glu Glu Arg Gln Asp
```

```
                145                 150                 155                 160
Leu Arg Arg Met Met Lys Arg Val Ile Gly Gly Thr Pro Lys Lys Val
                165                 170                 175

Pro Glu Glu Tyr Gln Trp Arg Thr Pro Phe Asp Gln Val Asn Lys Ile
                180                 185                 190

Gln Ala Pro Val Leu Leu Ile His Gly Glu Lys Asp Gln Asn Val Ser
                195                 200                 205

Ile Gln His Ser Tyr Leu Leu Glu Glu Lys Leu Lys Gln Leu His Lys
                210                 215                 220

Pro Val Glu Thr Trp Tyr Tyr Ser Thr Phe Thr His Tyr Phe Pro Pro
225                 230                 235                 240

Lys Glu Asn Arg Arg Ile Val Arg Gln Leu Thr Gln Trp Met Lys Asn
                245                 250                 255

<210> SEQ ID NO 3
<211> LENGTH: 255
<212> TYPE: PRT
<213> ORGANISM: Bacillus

<400> SEQUENCE: 3

Met Ile Gln Ile Glu Asn Gln Thr Val Ser Gly Ile Pro Phe Leu His
1               5                   10                  15

Ile Val Lys Glu Glu Asn Arg His Arg Ala Val Pro Leu Val Ile Phe
                20                  25                  30

Ile His Gly Phe Thr Ser Ala Lys Glu His Asn Leu His Ile Ala Tyr
            35                  40                  45

Leu Leu Ala Glu Lys Gly Phe Arg Ala Val Leu Pro Glu Ala Leu His
        50                  55                  60

His Gly Glu Arg Gly Glu Glu Met Ala Val Glu Glu Leu Ala Gly His
65                  70                  75                  80

Phe Trp Asp Ile Val Leu Asn Glu Ile Glu Ile Gly Val Leu Lys
                85                  90                  95

Asn His Phe Glu Lys Glu Gly Leu Ile Asp Gly Gly Arg Ile Gly Leu
                100                 105                 110

Ala Gly Thr Ser Met Gly Gly Ile Thr Thr Leu Gly Ala Leu Thr Ala
            115                 120                 125

Tyr Asp Trp Ile Lys Ala Gly Val Ser Leu Met Gly Ser Pro Asn Tyr
        130                 135                 140

Val Glu Leu Phe Gln Gln Ile Asp His Ile Gln Ser Gln Gly Ile
145                 150                 155                 160

Glu Ile Asp Val Pro Glu Glu Lys Val Gln Gln Leu Met Lys Arg Leu
                165                 170                 175

Glu Leu Arg Asp Leu Ser Leu Gln Pro Glu Lys Leu Gln Gln Arg Pro
                180                 185                 190

Leu Leu Phe Trp His Gly Ala Lys Asp Lys Val Val Pro Tyr Ala Pro
            195                 200                 205

Thr Arg Lys Phe Tyr Asp Thr Ile Lys Ser His Tyr Ser Glu Gln Pro
        210                 215                 220

Glu Arg Leu Gln Phe Ile Gly Asp Glu Asn Ala Asp His Lys Val Pro
225                 230                 235                 240

Arg Ala Ala Val Leu Lys Thr Ile Glu Trp Phe Glu Thr Tyr Leu
                245                 250                 255

<210> SEQ ID NO 4
<211> LENGTH: 300
```

```
<212> TYPE: PRT
<213> ORGANISM: Bacillus

<400> SEQUENCE: 4

Met Lys Lys Ile Leu Leu Ala Ile Gly Ala Leu Val Thr Ala Val Ile
 1               5                  10                  15

Ala Ile Gly Ile Val Phe Ser His Met Ile Leu Phe Ile Lys Lys Lys
                20                  25                  30

Thr Asp Glu Asp Ile Ile Lys Arg Glu Thr Asp Asn Gly His Asp Val
            35                  40                  45

Phe Glu Ser Phe Glu Gln Met Glu Lys Thr Ala Phe Val Ile Pro Ser
50                  55                  60

Ala Tyr Gly Tyr Asp Ile Lys Gly Tyr His Val Ala Pro His Asp Thr
65                  70                  75                  80

Pro Asn Thr Ile Ile Cys His Gly Val Thr Met Asn Val Leu Asn
                85                  90                  95

Ser Leu Lys Tyr Met His Leu Phe Leu Asp Leu Gly Trp Asn Val Leu
                100                 105                 110

Ile Tyr Asp His Arg Arg His Gly Gln Ser Gly Gly Lys Thr Thr Ser
                115                 120                 125

Tyr Gly Phe Tyr Glu Lys Asp Asp Leu Asn Lys Val Val Ser Leu Leu
130                 135                 140

Lys Asn Lys Thr Asn His Arg Gly Leu Ile Gly Ile His Gly Glu Ser
145                 150                 155                 160

Met Gly Ala Val Thr Ala Leu Leu Tyr Ala Gly Ala His Cys Ser Asp
                165                 170                 175

Gly Ala Asp Phe Tyr Ile Ala Asp Cys Pro Phe Ala Cys Phe Asp Glu
                180                 185                 190

Gln Leu Ala Tyr Arg Leu Arg Ala Glu Tyr Arg Leu Pro Ser Trp Pro
                195                 200                 205

Leu Leu Pro Ile Ala Asp Phe Phe Leu Lys Leu Arg Gly Gly Tyr Arg
                210                 215                 220

Ala Arg Glu Val Ser Pro Leu Ala Val Ile Asp Lys Ile Glu Lys Pro
225                 230                 235                 240

Val Leu Phe Ile His Ser Lys Asp Asp Asp Tyr Ile Pro Val Ser Ser
                245                 250                 255

Thr Glu Arg Leu Tyr Glu Lys Lys Arg Gly Pro Lys Ala Leu Tyr Ile
                260                 265                 270

Ala Glu Asn Gly Glu His Ala Met Ser Tyr Thr Lys Asn Arg His Thr
                275                 280                 285

Tyr Arg Lys Thr Val Gln Glu Phe Leu Asp Asn Met
                290                 295                 300

<210> SEQ ID NO 5
<211> LENGTH: 281
<212> TYPE: PRT
<213> ORGANISM: Bacillus

<400> SEQUENCE: 5

Met Glu Arg Ala Gly Ile Cys His Ser Asp Gly Phe Asp Leu Ala Tyr
 1               5                  10                  15

Arg Ile Glu Gly Glu Gly Ala Pro Ile Leu Val Ile Gly Ser Ala Ala
                20                  25                  30

Tyr Tyr Pro Arg Leu Phe Ser Ser Asp Ile Lys Gln Lys Tyr Gln Trp
                35                  40                  45
```

```
Val Phe Val Asp His Arg Gly Phe Ala Lys Pro Lys Arg Glu Leu Arg
 50                  55                  60

Ala Glu Asp Ser Arg Leu Asp Ala Val Leu Ala Asp Ile Glu Arg Met
 65                  70                  75                  80

Arg Thr Phe Leu Gln Leu Glu Asp Val Thr Thr Leu Gly His Ser Gly
                 85                  90                  95

His Ala Phe Met Ala Leu Glu Tyr Ala Arg Thr Tyr Pro Lys Gln Val
            100                 105                 110

Arg Lys Val Ala Leu Phe Asn Thr Ala Pro Asp Asn Ser Glu Glu Arg
        115                 120                 125

Gln Arg Lys Ser Glu Ser Phe Phe Met Glu Thr Ala Ser Leu Glu Arg
    130                 135                 140

Lys Lys Arg Phe Glu Lys Asp Ile Glu Asn Leu Pro Gln Asp Ile Asp
145                 150                 155                 160

Lys Asp Pro Glu Arg Arg Phe Val His Met Cys Ile Arg Ala Glu Ala
                165                 170                 175

Lys Ser Phe Tyr Gln Glu Arg Pro His Ala Ala Leu Trp Asp Gly
            180                 185                 190

Val Phe Thr Asn Met Pro Ile Ile Asp Glu Leu Trp Gly Asn Thr Phe
        195                 200                 205

Ala Arg Ile Asp Leu Leu Gln Arg Leu Ala Asp Val Arg Met Pro Val
    210                 215                 220

Tyr Ile Gly Leu Gly Arg Tyr Asp Tyr Leu Val Ala Pro Val Ser Leu
225                 230                 235                 240

Trp Asp Ala Val Asp Gly Leu Tyr Pro His Val Asp Lys Val Ile Phe
                245                 250                 255

Glu Lys Ser Gly His Gln Pro Met Leu Glu Pro Glu Ala Phe Asp
            260                 265                 270

Gln Ser Phe Arg Lys Trp Leu Asp Gln
            275                 280

<210> SEQ ID NO 6
<211> LENGTH: 298
<212> TYPE: PRT
<213> ORGANISM: Bacillus

<400> SEQUENCE: 6

Met Arg Ala Glu Arg Arg Lys Gln Leu Phe Arg Leu Leu Gly Asp Leu
 1               5                  10                  15

Pro Asp Arg Arg Pro Ile Ser Val Glu Thr Leu Arg Ile Glu Glu Arg
                20                  25                  30

Glu Glu Asn Ile Val Glu Thr Leu Leu Leu Asp Leu Asn Gly His Glu
            35                  40                  45

Lys Ala Pro Ala Tyr Phe Val Lys Pro Lys Lys Thr Glu Gly Pro Cys
 50                  55                  60

Pro Ala Val Leu Phe Gln His Ser His Gly Gly Gln Tyr Asp Arg Gly
 65                  70                  75                  80

Lys Ser Glu Leu Ile Glu Gly Ala Asp Tyr Leu Lys Thr Pro Ser Phe
                 85                  90                  95

Ser Asp Gly Leu Thr Ser Leu Gly Tyr Gly Val Leu Ala Ile Asp His
            100                 105                 110

Trp Gly Phe Gly Asp Arg Arg Gly Lys Ala Glu Ser Glu Ile Phe Lys
        115                 120                 125

Glu Met Leu Leu Thr Gly Lys Val Met Trp Gly Met Met Ile Tyr Asp
    130                 135                 140
```

```
Ser Leu Ser Ala Leu Asp Tyr Met Gln Ser Arg Ser Asp Val Gln Pro
145                 150                 155                 160

Asp Arg Ile Gly Thr Ile Gly Met Ser Met Gly Gly Leu Met Ala Trp
                165                 170                 175

Trp Thr Ala Ala Leu Asp Asp Arg Ile Lys Val Cys Val Asp Leu Cys
                180                 185                 190

Ser Gln Val Asp His His Val Leu Ile Lys Thr Gln Asn Leu Asp Arg
            195                 200                 205

His Gly Phe Tyr Tyr Val Pro Ser Leu Ala Lys His Phe Ser Ala
        210                 215                 220

Ser Glu Ile Gln Ser Leu Ile Ala Pro Arg Pro His Leu Ser Leu Val
225                 230                 235                 240

Gly Val His Asp Arg Leu Thr Pro Ala Glu Gly Val Asp Lys Ile Glu
                245                 250                 255

Lys Glu Leu Thr Ala Val Tyr Ala Gly Gln Gly Ala Ala Asp Cys Tyr
                260                 265                 270

Arg Val Val Arg Ser Ala Ser Gly His Phe Glu Thr Ala Val Ile Arg
                275                 280                 285

His Glu Ala Val Arg Phe Leu Gln Lys Trp
        290                 295
```

```
<210> SEQ ID NO 7
<211> LENGTH: 190
<212> TYPE: PRT
<213> ORGANISM: Bacillus

<400> SEQUENCE: 7

Met Thr Lys Gln Val Tyr Ile Ile His Gly Tyr Arg Ala Ser Ser Thr
1               5                   10                  15

Asn His Trp Phe Pro Trp Leu Lys Lys Arg Leu Leu Ala Asp Gly Val
                20                  25                  30

Gln Ala Asp Ile Leu Asn Met Pro Asn Pro Leu Gln Pro Arg Leu Glu
            35                  40                  45

Asp Trp Leu Asp Thr Leu Ser Leu Tyr Gln His Thr Leu His Glu Asn
    50                  55                  60

Thr Tyr Leu Val Ala His Ser Leu Gly Cys Pro Ala Ile Leu Arg Phe
65                  70                  75                  80

Leu Glu His Leu Gln Leu Arg Lys Gln Leu Gly Gly Ile Ile Leu Val
                85                  90                  95

Ser Gly Phe Ala Lys Ser Leu Pro Thr Leu Gln Met Leu Asp Glu Phe
                100                 105                 110

Thr Gln Gly Ser Phe Asp His Gln Lys Ile Ile Glu Ser Ala Lys His
            115                 120                 125

Arg Ala Val Ile Ala Ser Lys Asp Asp Gln Ile Val Pro Phe Ser Phe
    130                 135                 140

Ser Lys Asp Leu Ala Gln Gln Ile Asp Ala Ala Leu Tyr Glu Val Gln
145                 150                 155                 160

His Gly Gly His Phe Leu Glu Asp Glu Gly Phe Thr Ser Leu Pro Ile
                165                 170                 175

Val Tyr Asp Val Leu Thr Ser Tyr Phe Ser Lys Glu Thr Arg
                180                 185                 190
```

```
<210> SEQ ID NO 8
<211> LENGTH: 296
<212> TYPE: PRT
```

```
<213> ORGANISM: Bacillus

<400> SEQUENCE: 8

Met Ile Gln Asp Ser Met Gln Phe Ala Ala Val Glu Ser Gly Leu Arg
 1               5                  10                  15

Phe Tyr Gln Ala Tyr Asp Gln Ser Leu Ser Leu Trp Pro Ile Glu Ser
                20                  25                  30

Glu Ala Phe Tyr Val Ser Thr Arg Phe Gly Lys Thr His Ile Ile Ala
            35                  40                  45

Ser Gly Pro Lys Asp Ala Pro Ser Leu Ile Leu His Gly Gly Leu
        50                  55                  60

Phe Ser Ser Ala Met Trp Tyr Pro Asn Ile Ala Ala Trp Ser Ser Gln
65                  70                  75                  80

Phe Arg Thr Tyr Ala Val Asp Ile Ile Gly Asp Lys Asn Lys Ser Ile
                85                  90                  95

Pro Ser Ala Ala Met Glu Thr Arg Ala Asp Phe Ala Glu Trp Met Lys
            100                 105                 110

Asp Val Phe Asp Ser Leu Gly Leu Glu Thr Ala His Leu Ala Gly Leu
            115                 120                 125

Ser Leu Gly Gly Ser His Ile Val Asn Phe Leu Leu Arg Ala Pro Glu
        130                 135                 140

Arg Val Glu Arg Ala Val Val Ile Ser Pro Ala Glu Ala Phe Ile Ser
145                 150                 155                 160

Phe His Pro Asp Val Tyr Lys Tyr Ala Ala Glu Leu Thr Gly Ala Arg
                165                 170                 175

Gly Ala Glu Ser Tyr Ile Lys Trp Ile Thr Gly Asp Ser Tyr Asp Leu
            180                 185                 190

His Pro Leu Leu Gln Arg Gln Ile Val Ala Gly Val Glu Trp Gln Asp
            195                 200                 205

Glu Gln Arg Ser Leu Lys Pro Thr Glu Asn Gly Phe Pro Tyr Val Phe
        210                 215                 220

Thr Asp Gln Glu Leu Lys Ser Ile Gln Val Pro Val Leu Leu Met Phe
225                 230                 235                 240

Gly Glu His Glu Ala Met Tyr His Gln Met Ala Phe Glu Arg Ala
                245                 250                 255

Ser Val Leu Val Pro Gly Ile Gln Ala Glu Ile Val Lys Asn Ala Gly
            260                 265                 270

His Leu Leu Ser Leu Glu Gln Pro Glu Tyr Val Asn Gln Arg Val Leu
            275                 280                 285

Ser Phe Leu Cys Gly Gly Ile Lys
        290                 295

<210> SEQ ID NO 9
<211> LENGTH: 286
<212> TYPE: PRT
<213> ORGANISM: Bacillus

<400> SEQUENCE: 9

Met Asp Gly Val Lys Cys Gln Phe Val Asn Thr Asn Gly Ile Thr Leu
 1               5                  10                  15

His Val Ala Ala Ala Gly Arg Glu Asp Gly Pro Leu Ile Val Leu Leu
                20                  25                  30

His Gly Phe Pro Glu Phe Trp Tyr Gly Trp Lys Asn Gln Ile Lys Pro
            35                  40                  45

Leu Val Asp Ala Gly Tyr Arg Val Ile Ala Pro Asp Gln Arg Gly Tyr
```

```
            50                  55                  60
Asn Leu Ser Asp Lys Pro Glu Gly Ile Asp Ser Tyr Arg Ile Asp Thr
 65                  70                  75                  80

Leu Arg Asp Asp Ile Ile Gly Leu Ile Thr Gln Phe Thr Asp Glu Lys
                 85                  90                  95

Ala Ile Val Ile Gly His Asp Trp Gly Gly Ala Val Ala Trp His Leu
                100                 105                 110

Ala Ser Thr Arg Pro Glu Tyr Leu Glu Lys Leu Ile Ala Ile Asn Ile
                115                 120                 125

Pro His Pro His Val Met Lys Thr Val Thr Pro Leu Tyr Pro Pro Gln
130                 135                 140

Trp Leu Lys Ser Ser Tyr Ile Ala Tyr Phe Gln Leu Pro Asp Ile Pro
145                 150                 155                 160

Glu Ala Ser Leu Arg Glu Asn Asp Tyr Asp Thr Leu Asp Lys Ala Ile
                165                 170                 175

Gly Leu Ser Asp Arg Pro Ala Leu Phe Thr Ser Glu Asp Val Ser Arg
                180                 185                 190

Tyr Lys Glu Ala Trp Lys Gln Pro Gly Ala Leu Thr Ala Met Leu Asn
                195                 200                 205

Trp Tyr Arg Ala Leu Arg Lys Gly Ser Leu Ala Glu Lys Pro Ser Tyr
210                 215                 220

Glu Thr Val Pro Tyr Arg Met Ile Trp Gly Met Glu Asp Arg Phe Leu
225                 230                 235                 240

Ser Arg Lys Leu Ala Lys Glu Thr Glu Arg His Cys Pro Asn Gly His
                245                 250                 255

Leu Ile Phe Val Asp Glu Ala Ser His Trp Ile Asn His Glu Lys Pro
                260                 265                 270

Ala Ile Val Asn Gln Leu Ile Leu Glu Tyr Leu Lys Asn Gln
                275                 280                 285

<210> SEQ ID NO 10
<211> LENGTH: 271
<212> TYPE: PRT
<213> ORGANISM: Bacillus

<400> SEQUENCE: 10

Met Pro Tyr Ile Ile Leu Glu Asp Gln Thr Arg Leu Tyr Tyr Glu Thr
  1                   5                  10                  15

His Gly Ser Gly Thr Pro Ile Leu Phe Ile His Gly Val Leu Met Ser
                 20                  25                  30

Gly Gln Phe Phe His Lys Gln Phe Ser Val Leu Ser Ala Asn Tyr Gln
             35                  40                  45

Cys Ile Arg Leu Asp Leu Arg Gly His Gly Glu Ser Asp Lys Val Leu
         50                  55                  60

His Gly His Thr Ile Ser Gln Tyr Ala Arg Asp Ile Arg Glu Phe Leu
 65                  70                  75                  80

Asn Ala Met Glu Leu Asp His Val Val Leu Ala Gly Trp Ser Met Gly
                 85                  90                  95

Ala Phe Val Val Trp Asp Tyr Leu Asn Gln Phe Gly Asn Asp Asn Ile
                100                 105                 110

Gln Ala Ala Val Ile Ile Asp Gln Ser Ala Ser Asp Tyr Gln Trp Glu
                115                 120                 125

Gly Trp Glu His Gly Pro Phe Asp Phe Asp Gly Leu Lys Thr Ala Met
130                 135                 140
```

```
His Ala Ile Gln Thr Asp Pro Leu Pro Phe Tyr Glu Ser Phe Ile Gln
145                 150                 155                 160

Asn Met Phe Ala Glu Pro Pro Ala Glu Thr Glu Thr Glu Trp Met Leu
            165                 170                 175

Ala Glu Ile Leu Lys Gln Pro Ala Ala Ile Ser Ser Thr Ile Leu Phe
            180                 185                 190

Asn Gln Thr Ala Ala Asp Tyr Arg Gly Thr Leu Gln Asn Ile Asn Val
            195                 200                 205

Pro Ala Leu Leu Cys Phe Gly Glu Asp Lys Lys Phe Phe Ser Thr Ala
210                 215                 220

Ala Gly Glu His Leu Arg Ser Asn Ile Pro Asn Ala Thr Leu Val Thr
225                 230                 235                 240

Phe Pro Lys Ser Ser His Cys Pro Phe Leu Glu Pro Asp Ala Phe
                245                 250                 255

Asn Ser Thr Leu Leu Ser Phe Leu Asp Gly Val Ile Gly Lys Ser
            260                 265                 270

<210> SEQ ID NO 11
<211> LENGTH: 269
<212> TYPE: PRT
<213> ORGANISM: Bacillus

<400> SEQUENCE: 11

Met Asn Glu Ala Ile Leu Ser Arg Asn His Val Lys Val Lys Gly Ser
1               5                   10                  15

Gly Lys Ala Ser Ile Met Phe Ala Pro Gly Phe Gly Cys Asp Gln Ser
            20                  25                  30

Val Trp Asn Ala Val Ala Pro Ala Phe Glu Glu Asp His Arg Val Ile
            35                  40                  45

Leu Phe Asp Tyr Val Gly Ser Gly His Ser Asp Leu Arg Ala Tyr Asp
    50                  55                  60

Leu Asn Arg Tyr Gln Thr Leu Asp Gly Tyr Ala Gln Asp Val Leu Asp
65                  70                  75                  80

Val Cys Glu Ala Leu Asp Leu Lys Glu Thr Val Phe Val Gly His Ser
                85                  90                  95

Val Gly Ala Leu Ile Gly Met Leu Ala Ser Ile Arg Arg Pro Glu Leu
            100                 105                 110

Phe Ser His Leu Val Met Val Gly Pro Ser Pro Cys Tyr Leu Asn Asp
            115                 120                 125

Pro Pro Glu Tyr Tyr Gly Gly Phe Glu Glu Glu Gln Leu Leu Gly Leu
130                 135                 140

Leu Glu Met Met Glu Lys Asn Tyr Ile Gly Trp Ala Thr Val Phe Ala
145                 150                 155                 160

Ala Thr Val Leu Asn Gln Pro Asp Arg Pro Glu Ile Lys Glu Glu Leu
            165                 170                 175

Glu Ser Arg Phe Cys Ser Thr Asp Pro Val Ile Ala Arg Gln Phe Ala
            180                 185                 190

Lys Ala Ala Phe Phe Ser Asp His Arg Glu Asp Leu Ser Lys Val Thr
            195                 200                 205

Val Pro Ser Leu Ile Leu Gln Cys Ala Asp Asp Ile Ile Ala Pro Ala
            210                 215                 220

Thr Val Gly Lys Tyr Met His Gln His Leu Pro Tyr Ser Ser Leu Lys
225                 230                 235                 240

Gln Met Glu Ala Arg Gly His Cys Pro His Met Ser His Pro Asp Glu
                245                 250                 255
```

-continued

Thr Ile Gln Leu Ile Gly Asp Tyr Leu Lys Ala His Val
         260                 265

<210> SEQ ID NO 12
<211> LENGTH: 256
<212> TYPE: PRT
<213> ORGANISM: Bacillus

<400> SEQUENCE: 12

Met Pro Leu Ile Ser Ile Asp Ser Arg Lys His Leu Phe Tyr Glu Glu
 1               5                  10                  15

Tyr Gly Gln Gly Ile Pro Ile Ile Phe Ile His Pro Pro Gly Met Gly
            20                  25                  30

Arg Lys Val Phe Tyr Tyr Gln Arg Leu Leu Ser Lys His Phe Arg Val
        35                  40                  45

Ile Phe Pro Asp Leu Ser Gly His Gly Asp Ser Asp His Ile Asp Gln
 50                  55                  60

Pro Ala Ser Ile Ser Tyr Tyr Ala Asn Glu Ile Ala Gln Phe Met Asp
 65                  70                  75                  80

Ala Leu His Ile Asp Lys Ala Val Leu Phe Gly Tyr Ser Ala Gly Gly
                85                  90                  95

Leu Ile Ala Gln His Ile Gly Phe Thr Arg Pro Asp Lys Val Ser His
            100                 105                 110

Leu Ile Leu Ser Gly Ala Tyr Pro Ala Val His Asn Val Ile Gly Gln
        115                 120                 125

Lys Leu His Lys Leu Gly Met Tyr Leu Leu Glu Lys Asn Pro Gly Leu
130                 135                 140

Leu Met Lys Ile Leu Ala Gly Ser His Thr Lys Asp Arg Gln Leu Arg
145                 150                 155                 160

Ser Ile Leu Thr Asp His Met Lys Lys Ala Asp Gln Ala His Trp His
                165                 170                 175

Gln Tyr Tyr Leu Asp Ser Leu Gly Tyr Asn Cys Ile Glu Gln Leu Pro
            180                 185                 190

Arg Leu Glu Met Pro Met Leu Phe Met Tyr Gly Gly Leu Arg Asp Trp
        195                 200                 205

Thr Phe Thr Asn Ala Gly Tyr Tyr Arg Arg Ser Cys Arg His Ala Glu
    210                 215                 220

Phe Phe Arg Leu Glu Tyr Gln Gly His Gln Leu Pro Thr Lys Gln Trp
225                 230                 235                 240

Lys Thr Cys Asn Glu Leu Val Thr Gly Phe Val Leu Thr His Ser
                245                 250                 255

<210> SEQ ID NO 13
<211> LENGTH: 253
<212> TYPE: PRT
<213> ORGANISM: Bacillus

<400> SEQUENCE: 13

Met Lys Ser Ala Trp Met Glu Lys Thr Tyr Thr Ile Asp Gly Cys Ala
 1               5                  10                  15

Phe His Thr Gln His Arg Lys Gly Ser Ser Gly Val Thr Ile Val Phe
            20                  25                  30

Glu Ala Gly Tyr Gly Thr Ser Ser Glu Thr Trp Lys Pro Leu Met Ala
        35                  40                  45

Asp Ile Asp Asp Glu Phe Gly Ile Phe Thr Tyr Asp Arg Ala Gly Ile
 50                  55                  60

```
Gly Lys Ser Gly Gln Ser Arg Ala Lys Arg Thr Ala Asp Gln Gln Val
 65                  70                  75                  80

Lys Glu Leu Glu Ser Leu Leu Lys Ala Ala Asp Val Lys Pro Pro Tyr
                 85                  90                  95

Leu Ala Val Ser His Ser Tyr Gly Ala Val Ile Thr Gly Leu Trp Ala
            100                 105                 110

Cys Lys Asn Lys His Asp Ile Ile Gly Met Val Leu Asp Pro Ala
            115                 120                 125

Leu Gly Asp Cys Ala Ser Phe Thr Phe Ile Pro Glu Glu Met His Lys
130                 135                 140

Ser His Thr Arg Lys Met Met Leu Glu Gly Thr His Ala Glu Phe Ser
145                 150                 155                 160

Lys Ser Leu Gln Glu Leu Lys Lys Arg Gln Val His Leu Gly Asn Met
                165                 170                 175

Pro Leu Leu Val Leu Ser Ser Gly Glu Arg Thr Glu Lys Phe Ala Ala
                180                 185                 190

Glu Gln Glu Trp Gln Asn Leu His Ser Ser Ile Leu Ser Leu Ser Asn
            195                 200                 205

Gln Ser Gly Trp Ile Gln Ala Lys Asn Ser Ser His Asn Ile His His
        210                 215                 220

Asp Glu Pro His Ile Val His Leu Ala Ile Tyr Asp Val Trp Cys Ala
225                 230                 235                 240

Ala Cys Gln Gln Ala Ala Pro Leu Tyr Gln Ala Val Asn
                245                 250

<210> SEQ ID NO 14
<211> LENGTH: 242
<212> TYPE: PRT
<213> ORGANISM: Bacillus

<400> SEQUENCE: 14

Met Ser Gln Leu Phe Lys Ser Phe Asp Ala Ser Glu Lys Thr Gln Leu
  1               5                  10                  15

Ile Cys Phe Pro Phe Ala Gly Gly Tyr Ser Ala Ser Phe Arg Pro Leu
                 20                  25                  30

His Ala Phe Leu Gln Gly Glu Cys Glu Met Leu Ala Ala Glu Pro Pro
             35                  40                  45

Gly His Gly Thr Asn Gln Thr Ser Ala Ile Glu Asp Leu Glu Glu Leu
         50                  55                  60

Thr Asp Leu Tyr Lys Gln Glu Leu Asn Leu Arg Pro Asp Arg Pro Phe
 65                  70                  75                  80

Val Leu Phe Gly His Ser Met Gly Gly Met Ile Thr Phe Arg Leu Ala
                 85                  90                  95

Gln Lys Leu Glu Arg Glu Gly Ile Phe Pro Gln Ala Val Ile Ile Ser
            100                 105                 110

Ala Ile Gln Pro Pro His Ile Gln Arg Lys Val Ser His Leu Pro
            115                 120                 125

Asp Asp Gln Phe Leu Asp His Ile Ile Gln Leu Gly Gly Met Pro Ala
130                 135                 140

Glu Leu Val Glu Asn Lys Glu Val Met Ser Phe Leu Pro Ser Phe
145                 150                 155                 160

Arg Ser Asp Tyr Arg Ala Leu Glu Gln Phe Glu Leu Tyr Asp Leu Ala
                165                 170                 175

Gln Ile Gln Ser Pro Val His Val Phe Asn Gly Leu Asp Asp Lys Lys
```

```
                        180                 185                 190
Cys Ile Arg Asp Ala Glu Gly Trp Lys Lys Trp Ala Lys Asp Ile Thr
            195                 200                 205

Phe His Gln Phe Asp Gly Gly His Met Phe Leu Leu Ser Gln Thr Glu
    210                 215                 220

Glu Val Ala Glu Arg Ile Phe Ala Ile Leu Asn Gln His Pro Ile Ile
225                 230                 235                 240

Gln Pro

<210> SEQ ID NO 15
<211> LENGTH: 256
<212> TYPE: PRT
<213> ORGANISM: Bacillus

<400> SEQUENCE: 15

Met His Gly Gly His Ser Asn Cys Tyr Glu Glu Phe Gly Tyr Thr Ala
1               5                   10                  15

Leu Ile Glu Gln Gly Tyr Ser Ile Ile Thr Pro Ser Arg Pro Gly Tyr
            20                  25                  30

Gly Arg Thr Ser Lys Glu Ile Gly Lys Ser Leu Ala Asn Ala Cys Arg
        35                  40                  45

Phe Tyr Val Lys Leu Leu Asp His Leu Gln Ile Glu Ser Val His Val
    50                  55                  60

Ile Ala Ile Ser Ala Gly Gly Pro Ser Gly Ile Cys Phe Ala Ser His
65                  70                  75                  80

Tyr Pro Glu Arg Val Asn Thr Leu Thr Leu Gln Ser Ala Val Thr Lys
                85                  90                  95

Glu Trp Leu Thr Pro Lys Asp Thr Glu Tyr Lys Leu Gly Glu Ile Leu
            100                 105                 110

Phe Arg Pro Pro Val Glu Lys Trp Ile Trp Lys Leu Ile Ser Ser Leu
        115                 120                 125

Asn Asn Ala Phe Pro Arg Leu Met Phe Arg Ala Met Ser Pro Gln Phe
    130                 135                 140

Ser Thr Leu Pro Phe Gln Arg Ile Lys Ser Leu Met Asn Glu Lys Asp
145                 150                 155                 160

Ile Glu Ala Phe Arg Lys Met Asn Ser Arg Gln Arg Ser Gly Glu Gly
                165                 170                 175

Phe Leu Ile Asp Leu Ser Gln Thr Ala Ala Val Ser Leu Lys Asp Leu
            180                 185                 190

Gln Ala Ile Ile Cys Pro Val Leu Ile Met Gln Ser Val Tyr Asp Gly
        195                 200                 205

Leu Val Asp Leu Ser His Ala His Ala Lys Glu His Ile Arg Gly
    210                 215                 220

Ala Val Leu Cys Leu Leu His Ser Trp Gly His Leu Ile Trp Leu Gly
225                 230                 235                 240

Lys Glu Ala Ala Glu Thr Gly Ser Ile Leu Leu Gly Phe Leu Glu Ser
                245                 250                 255

<210> SEQ ID NO 16
<211> LENGTH: 318
<212> TYPE: PRT
<213> ORGANISM: Bacillus

<400> SEQUENCE: 16

Met Ile Pro Glu Lys Lys Ser Ile Ala Ile Met Lys Glu Leu Ser Ile
1               5                   10                  15
```

Gly Asn Thr Lys Gln Met Leu Met Ile Asn Gly Val Asp Val Lys Asn
                20                  25                  30

Pro Leu Leu Leu Phe Leu His Gly Gly Pro Gly Thr Pro Gln Ile Gly
            35                  40                  45

Tyr Val Arg His Tyr Gln Lys Glu Leu Glu Gln Tyr Phe Thr Val Val
        50                  55                  60

His Trp Asp Gln Arg Gly Ser Gly Leu Ser Tyr Ser Lys Arg Ile Ser
65                  70                  75                  80

His His Ser Met Thr Ile Asn His Phe Ile Lys Asp Thr Ile Gln Val
                85                  90                  95

Thr Gln Trp Leu Leu Ala His Phe Ser Lys Ser Lys Leu Tyr Leu Ala
            100                 105                 110

Gly His Ser Trp Gly Ser Ile Leu Ala Leu His Val Leu Gln Gln Arg
        115                 120                 125

Pro Asp Leu Phe Tyr Thr Tyr Tyr Gly Ile Ser Gln Val Val Asn Pro
    130                 135                 140

Gln Asp Glu Glu Ser Thr Ala Tyr Gln His Ile Arg Glu Ile Ser Glu
145                 150                 155                 160

Ser Lys Lys Ala Ser Ile Leu Ser Phe Leu Thr Arg Phe Ile Gly Ala
                165                 170                 175

Pro Pro Trp Lys Gln Asp Ile Gln His Leu Ile Tyr Arg Phe Cys Val
            180                 185                 190

Glu Leu Thr Arg Gly Gly Phe Thr His Arg His Arg Gln Ser Leu Ala
        195                 200                 205

Val Leu Phe Gln Met Leu Thr Gly Asn Glu Tyr Gly Val Arg Asn Met
    210                 215                 220

His Ser Phe Leu Asn Gly Leu Arg Phe Ser Lys Lys His Leu Thr Asp
225                 230                 235                 240

Glu Leu Tyr Arg Phe Asn Ala Phe Thr Ser Val Pro Ser Ile Lys Val
                245                 250                 255

Pro Cys Val Phe Ile Ser Gly Lys His Asp Leu Ile Val Pro Ala Glu
            260                 265                 270

Ile Ser Lys Gln Tyr Tyr Gln Glu Leu Glu Ala Pro Glu Lys Arg Trp
        275                 280                 285

Phe Gln Phe Glu Asn Ser Ala His Thr Pro His Ile Glu Glu Pro Ser
    290                 295                 300

Leu Phe Ala Asn Thr Leu Ser Arg His Ala Arg Asn His Leu
305                 310                 315

<210> SEQ ID NO 17
<211> LENGTH: 314
<212> TYPE: PRT
<213> ORGANISM: Bacillus

<400> SEQUENCE: 17

Met Arg Cys Leu Val Asp Ser Glu Asn His Tyr His Thr Leu Arg Phe
1               5                   10                  15

Ser Leu Arg Arg Gly Met Ser Tyr Cys Met Lys Glu Gln Thr Thr Asp
                20                  25                  30

Arg Thr Asn Gly Gly Thr Ser Asn Ala Phe Thr Ile Pro Gly Thr Glu
            35                  40                  45

Val Arg Met Met Ser Ser Arg Asn Glu Asn Arg Thr Tyr His Ile Phe
        50                  55                  60

Ile Ser Lys Pro Ser Thr Pro Pro Pro Ala Gly Tyr Pro Val Ile

-continued

```
                65                  70                  75                  80

Tyr Leu Leu Asp Ala Asn Ser Val Phe Gly Thr Met Thr Glu Ala Val
                        85                  90                  95

Arg Ile Gln Gly Arg Arg Pro Glu Lys Thr Gly Val Ile Pro Ala Val
                    100                 105                 110

Ile Val Gly Ile Gly Tyr Glu Thr Ala Glu Pro Phe Ser Ser Ala Arg
                    115                 120                 125

His Arg Asp Phe Thr Met Pro Thr Ala Gln Ser Lys Leu Pro Glu Arg
            130                 135                 140

Pro Asp Gly Arg Glu Trp Pro Glu His Gly Gly Ala Glu Gly Phe Phe
145                 150                 155                 160

Arg Phe Ile Glu Glu Asp Leu Lys Pro Glu Ile Glu Arg Asp Tyr Gln
                        165                 170                 175

Ile Asp Lys Lys Arg Gln Thr Ile Phe Gly His Ser Leu Gly Gly Leu
                    180                 185                 190

Phe Val Leu Gln Val Leu Leu Thr Lys Pro Asp Ala Phe Gln Thr Tyr
                    195                 200                 205

Ile Ala Gly Ser Pro Ser Ile His Trp Asn Lys Pro Phe Ile Leu Lys
            210                 215                 220

Lys Thr Asp His Phe Val Ser Leu Thr Lys Lys Asn Asn Gln Pro Ile
225                 230                 235                 240

Asn Ile Leu Leu Ala Ala Gly Glu Leu Glu Gln His His Lys Ser Arg
                    245                 250                 255

Met Asn Asp Asn Ala Arg Glu Leu Tyr Glu Arg Leu Ala Val Leu Ser
                260                 265                 270

Glu Gln Gly Ile Arg Ala Glu Phe Cys Glu Phe Ser Gly Glu Gly His
            275                 280                 285

Ile Ser Val Leu Pro Val Leu Val Ser Arg Ala Leu Arg Phe Ala Leu
            290                 295                 300

His Pro Asp Gly Pro His Leu Ser Met Gly
305                 310

<210> SEQ ID NO 18
<211> LENGTH: 200
<212> TYPE: PRT
<213> ORGANISM: Bacillus

<400> SEQUENCE: 18

Met Lys His Ile Tyr Glu Lys Gly Thr Ser Asp Asn Val Leu Leu Leu
  1               5                  10                  15

Leu His Gly Thr Gly Gly Asn Glu His Asp Leu Leu Ser Leu Gly Arg
                 20                  25                  30

Phe Ile Asp Pro Asp Ala His Leu Leu Gly Val Arg Gly Ser Val Leu
             35                  40                  45

Glu Asn Gly Met Pro Arg Phe Phe Lys Arg Leu Ser Glu Gly Val Phe
         50                  55                  60

Asp Glu Lys Asp Leu Val Val Arg Thr Arg Glu Leu Lys Asp Phe Ile
65                  70                  75                  80

Asp Glu Ala Ala Glu Thr His Gln Phe Asn Arg Gly Arg Val Ile Ala
                 85                  90                  95

Val Gly Tyr Ser Asn Gly Ala Asn Ile Ala Ala Ser Leu Leu Phe His
                100                 105                 110

Tyr Lys Asp Val Leu Lys Gly Ala Ile Leu His His Pro Met Val Pro
            115                 120                 125
```

Ile Arg Gly Ile Glu Leu Pro Asp Met Ala Gly Leu Pro Val Phe Ile
            130                 135                 140

Gly Ala Gly Lys Tyr Asp Pro Leu Cys Thr Lys Glu Glu Ser Glu Glu
145                 150                 155                 160

Leu Tyr Arg Tyr Leu Arg Asp Ser Gly Ala Ser Ala Ser Val Tyr Trp
                165                 170                 175

Gln Asp Gly Gly His Gln Leu Thr Gln His Glu Ala Glu Gln Ala Arg
            180                 185                 190

Glu Trp Tyr Lys Glu Ala Ile Val
                195                 200

<210> SEQ ID NO 19
<211> LENGTH: 240
<212> TYPE: PRT
<213> ORGANISM: Bacillus

<400> SEQUENCE: 19

Met Ala Pro Lys Asn Gly Thr Val Gln Glu Lys Lys Phe Phe Ser Lys
1               5                   10                  15

Glu Leu Asn Glu Glu Met Thr Leu Leu Val Tyr Leu Pro Ser Asn Tyr
                20                  25                  30

Ser Pro Leu Tyr Lys Tyr His Val Ile Ile Ala Gln Asp Gly His Asp
            35                  40                  45

Tyr Phe Arg Leu Gly Arg Ile Gly Arg Gln Val Glu Glu Leu Leu Ser
    50                  55                  60

Lys Arg Glu Ile Asp Arg Ser Ile Ile Ile Gly Val Pro Tyr Lys Asp
65                  70                  75                  80

Val Lys Glu Arg Arg Asn Thr Tyr His Pro Glu Gly Ser Lys Phe Ser
                85                  90                  95

Ala Tyr Lys Arg Phe Ile Ala His Glu Leu Val Pro Phe Ala Asp Asp
            100                 105                 110

Glu Tyr Pro Thr Tyr Gln Ile Gly Tyr Gly Arg Thr Leu Ile Gly Asp
        115                 120                 125

Ser Leu Gly Ala Thr Val Ser Leu Met Thr Ala Leu Asp Tyr Pro Asn
    130                 135                 140

Met Phe Gly Asn Ile Ile Met Gln Ser Pro Tyr Val Asp Lys His Val
145                 150                 155                 160

Leu Glu Ala Val Lys Gln Ser Asp Asp Ile Lys His Leu Ser Ile Tyr
                165                 170                 175

His Gln Ile Gly Thr Lys Glu Thr Asp Val His Thr Thr Asp Gly Asn
            180                 185                 190

Ile Leu Asp Phe Thr Glu Pro Asn Arg Glu Leu Lys Gln Leu Leu Glu
        195                 200                 205

Lys Lys Leu Ser Asp Tyr Asp Phe Glu Pro Phe Asp Gly Asp His Lys
    210                 215                 220

Trp Thr Tyr Trp Gln Pro Leu Ile Thr Pro Ala Leu Lys Lys Met Leu
225                 230                 235                 240

<210> SEQ ID NO 20
<211> LENGTH: 233
<212> TYPE: PRT
<213> ORGANISM: Bacillus

<400> SEQUENCE: 20

Met Ser Arg Tyr Leu Glu Met Leu Ser Leu Phe Gly Val Ala Gly Ala
1               5                   10                  15

```
His Pro Gly Gly Leu Ala Phe Ser Lys Ala Val Leu Gln Lys Ala Ala
              20                  25                  30

Pro Ser Pro Asp Gln Pro Ile Leu Asp Ala Gly Cys Gly Thr Gly Gln
         35                  40                  45

Thr Ala Ala Tyr Leu Gly His Leu Leu Tyr Pro Val Thr Val Val Asp
     50                  55                  60

Lys Asp Pro Ile Met Leu Glu Lys Ala Lys Arg Phe Ala Asn Glu
 65                  70                  75                  80

Gly Leu Ala Ile Pro Ala Tyr Gln Ala Glu Leu Glu His Leu Pro Phe
                 85                  90                  95

Ser Ser Glu Ser Phe Ser Cys Val Leu Ser Glu Ser Val Leu Ser Phe
                100                 105                 110

Ser Arg Leu Thr Ser Ser Leu Gln Glu Ile Ser Arg Val Leu Lys Pro
             115                 120                 125

Ser Gly Met Leu Ile Gly Ile Glu Ala Ala Leu Lys Lys Pro Met Pro
         130                 135                 140

Pro Ala Glu Lys Lys Gln Met Met Asp Phe Tyr Gly Phe Thr Cys Leu
145                 150                 155                 160

His Glu Glu Ser Glu Trp His Lys Leu Leu Arg Ser Tyr Gly Phe Gln
                165                 170                 175

Lys Thr Glu Ala Met Ser Leu Leu Pro Glu Asp Met Glu Phe Glu Pro
            180                 185                 190

Thr Thr Glu Met Asp Leu Ser Gln Thr Ile Asp Pro Ile Tyr Tyr Asp
        195                 200                 205

Thr Leu Gln Thr His Tyr Gln Leu Met Gln Leu Tyr Ser Glu Tyr Met
    210                 215                 220

Gly His Cys Ile Phe Ile Ala Tyr Lys
225                 230

<210> SEQ ID NO 21
<211> LENGTH: 259
<212> TYPE: PRT
<213> ORGANISM: Bacillus

<400> SEQUENCE: 21

Met Trp Thr Trp Lys Ala Asp Arg Pro Val Ala Val Ile Val Ile Ile
  1                   5                  10                  15

His Gly Ala Ser Glu Tyr His Gly Arg Tyr Lys Trp Leu Ile Glu Met
             20                  25                  30

Trp Arg Ser Ser Gly Tyr His Val Val Met Gly Asp Leu Pro Gly Gln
         35                  40                  45

Gly Thr Thr Thr Arg Ala Arg Gly His Ile Arg Ser Phe Gln Glu Tyr
     50                  55                  60

Ile Asp Glu Val Asp Ala Trp Ile Asp Lys Ala Arg Thr Phe Asp Leu
 65                  70                  75                  80

Pro Val Phe Leu Leu Gly His Ser Met Gly Gly Leu Val Ala Ile Glu
                 85                  90                  95

Trp Val Lys Gln Gln Arg Asn Pro Arg Ile Thr Gly Ile Ile Leu Ser
                100                 105                 110

Ser Pro Cys Leu Gly Leu Gln Ile Lys Val Asn Lys Ala Leu Asp Leu
            115                 120                 125

Ala Ser Lys Gly Leu Asn Val Ile Ala Pro Ser Leu Lys Val Asp Ser
        130                 135                 140

Gly Leu Ser Ile Asp Met Ala Thr Arg Asn Glu Asp Val Ile Glu Ala
145                 150                 155                 160
```

```
Asp Gln Asn Asp Ser Leu Tyr Val Arg Lys Val Ser Val Arg Trp Tyr
                165                 170                 175

Arg Glu Leu Leu Lys Thr Ile Glu Ser Ala Met Val Pro Thr Glu Ala
            180                 185                 190

Phe Leu Lys Val Pro Leu Leu Val Met Gln Ala Gly Asp Asp Lys Leu
        195                 200                 205

Val Asp Lys Thr Met Val Ile Lys Trp Phe Asn Gly Val Ala Ser His
    210                 215                 220

Asn Lys Ala Tyr Arg Glu Trp Glu Gly Leu Tyr His Glu Ile Phe Asn
225                 230                 235                 240

Glu Pro Glu Arg Glu Asp Val Phe Lys Ala Ala Arg Ala Phe Thr Asp
                245                 250                 255

Gln Tyr Ile
```

ALPHA/BETA HYDROLASE-FOLD ENZYMES

FIELD OF THE INVENTION

The present invention relates to alpha/beta hydrolase-fold enzymes derived from gram-positive microorganisms. The present invention provides the nucleic acid and amino acid sequences for the hydrolases and methods for their use.

BACKGROUND OF THE INVENTION

The alpha/beta hydrolase fold common to several hydrolytic enzymes of differing phylogenetic origin and catalytic function was described by Ollis et al. (1992, Protein Eng. 5(3):197–211). The core of each enzyme in this family was described as being similar: an alpha/beta sheet of eight beta-sheets connected by alpha-helices with conserved arrangement of catalytic residues. Members of this family were found to have a catalytic triad which is borne on the conserved loop structure found in the fold. In the five members discussed in Ollis et al., the catalytic residues always occur in the same order in the primary sequence: nucleophile, acid, histidine. Furthermore, the catalytic triad residues of the members had similar topological and three dimensional positions.

Members of the hydrolase family include a hydroxylyase (Wajant, et al., 1996, J. Biol. Chem. 271(42):25830–25834) which comprises the active site motif Gly-X-Ser-X-Gly/Ala and the residues Serine 80, Aspartic 208, and Histidine 236 which are critical for enzyme activity; 2-hydroxymuconic semialdehyde hydrolase, XylF (Diaz E., 1995, J. Biol. Chem. 270(11):6403–6411), which comprises the residues Ser107, Asp228 and His 256; non-heme haloperoxidases comprises oxidases, which perform halogenation and which are related to esterases (Pelletier et al., 1995, Biochim Biophys Acta, 1995,1250(2):149–157) which comprises the residues Serine 97, Aspartic acid 229, Histidine 258; and dipeptidyl-peptidase IV (David et al., 1993, J. Biol. Chem. 268(23):17247–17252), which comprises the residues Ser624Asp702, His734).

SUMMARY OF THE INVENTION

The present invention relates to the identification of gram-positive microorganism members of the family of alpha/beta hydrolase fold enzymes which are characterized by structural relatedness and which comprises conserved catalytic triads. These newly identified members of this family can be used in industrial applications, e.g., the textile industry, in cleaning compositions, such as detergents, and in animal feeds.

Accordingly, the present invention provides compositions comprising a hydrolase selected from the group consisting of YUXL, YTMA, YITV, YQKD, YCLE, YTAP, YDEN, YBFK, YFHM, YDJP, YVFQ, YVAM, YQJL, SRFAD, YCGS, YTPA, YBAC, YUII, YODD, YJCH, YODH which can be used in detergent compositions, compositions for the treatment of textiles; and animal feeds, for example. The present invention also provides commercial applications of the compositions, e.g., their use in methods for treating textiles and methods for cleaning.

The present invention provides amino acid sequences for hydrolases obtainable from B. subtilis (B. subtilis hydrolases). Due to the degeneracy of the genetic code, the present invention encompasses any nucleic acid sequence that encodes the specific hydrolase amino acid sequence shown in the Sequences.

The present invention provides methods for detecting gram positive microorganism homologs of the B. subtilis hydrolases that comprise hybridizing part or all of the nucleic acid encoding the hydrolase with nucleic acid derived from gram-positive organisms, either of genomic or cDNA origin. In one embodiment, the gram-positive microorganism includes *B. licheniformis, B. lentus, B. brevis, B. stearothermophilus, B. alkalophilus, B. amyloliquefaciens, B. coagulans, B. circulans, B. lautus* and *Bacillus thuringiensis*.

The invention further provides for a hydrolase that has at least 80%, at least 85%, at least 90%, and at least 95% homology with the specific amino acid sequences shown in the sequences. The invention also provides for a nucleic acid which encodes a hydrolase that has at least 80%, at least 85%, at least 90% and at least 95% homology with the naturally occurring nucleic acid sequence found in Bacillus subtilis.

In a preferred embodiment, the present invention provides the naturally occurring hydrolase nucleic acid molecule having the sequence found in Bacillus subtilis 1–168 strain (Bacillus Genetic Stock Center, accession number 1A1, Columbus, Ohio) as disclosed infra.

The present invention provides expression vectors and host cells comprising a nucleic acid encoding a gram positive hydrolase. The present invention also provides methods of making the gram positive hydrolase.

The present invention encompasses novel amino acid variations of hydrolase amino acid sequences from gram positive microorganisms disclosed herein that have hydrolytic activity. Naturally occurring hydrolases derived from gram positive microorganisms disclosed herein as well as proteolytically active amino acid variations or derivatives thereof, have application in the textile industry, in cleaning compositions and methods and in animal feed compositions.

In another embodiment, a host cell is engineered to produce a hydrolase of the present invention. In a further aspect of the present invention, a hydrolase from a gram positive microorganism is produced on an industrial fermentation scale in a host expression system. The host cell may be a gram-negative or gram-positive microorganism, a fungal organism, or higher Eucaryotes. Gram negative microorganisms include but are not limited to members of Enterobacteriaceae; gram positive microorganisms include but are not limited to members of Bacillus and Pseudomonase; fungal organisms include but are not limited to Aspergillus and Tricoderma; and higher eucaryotes include mammalian cells.

The gram positive microorganism host cell may be normally sporulating or non-sporulating and may be modified in other ways to facilitate expression of the hydrolase. In a preferred embodiment, the gram positive host cell is a Bacillus. In another embodiment, the Bacillus includes *B. subtilis, B. licheniformis, B. lentus, B. brevis, B. stearothermophilus, B. alkalophilus, B. amyloliquefaciens, B. coagulans, B. circulans, B. lautus and B. thuringiensis*. In a further preferred embodiment, the Bacillus host cell is Bacillus subtilis.

DETAILED DESCRIPTION

Definitions

The present invention relates to a newly characterized hydrolases from gram positive organisms. In a preferred embodiment, the gram positive organisms is a Bacillus. In another is preferred embodiment, the Bacillus includes *B. subtilis, B. licheniformis, B. lentus, B. brevis, B.*

*stearothermophilus, B. alkalophilus, B. amyloliquefaciens, B. coagulans, B. circulans, B. lautus* and *B. thuringiensis*.

In another preferred embodiment, the gram positive organism is Bacillus subtilis and the hydrolases have the amino acid sequence disclosed in the Sequences. In a preferred embodiment, the hydrolase is encoded by the naturally occurring nucleic acid that is found at the respective positions of B. subtilis detailed infra.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homologue" as used herein refers to a gram positive microorganism polynucleotide that has at least 80%, at least 85%, at least 90% and more preferably at least 95% identity to *B.subtilis* hydrolase, or which is capable of hybridizing to *B.subtilis* hydrolase under conditions of high stringency and which encodes an amino acid sequence having hydrolase activity.

The terms "isolated" or "purified" as used herein refer to a nucleic acid or peptide or protein that is removed from at least one component with which it is naturally associated. As used herein, isolated nucleic acid can include a vector comprising the nucleic acid.

As used herein, the term "overexpressing" when referring to the production of a protein in a host cell means that the protein is produced in greater amounts than in its naturally occurring environment.

As used herein, the phrase "hydrolytic activity" refers to a protein that is able to hydrolyze a peptide bond. Enzymes having proteolytic activity are described in Enzyme Nomenclature, 1992, edited Webb Academic Press, Inc.

I. Hydrolase Sequences

The present invention encompasses the use of hydrolase polynucleotide homologues encoding gram positive microorganism hydrolases which have at least 80%, at least 85%, at least 90%, and at least 95% identity to naturally occurring *B. subtilis* hydrolase nucleic acid as long as the homologue encodes a protein that has hydrolytic activity.

Gram positive polynucleotide homologues of *B. subtilis* hydrolase may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA.

As will be understood by those of skill in the art, the amino acid sequence disclosed in the Sequences may reflect inadvertent errors inherent to nucleic acid sequencing technology. The present invention encompasses the naturally occurring nucleic acid molecule having the nucleic acid sequence obtained from the genomic sequence of Bacillus species and the naturally occurring amino acid sequence.

Nucleic acid encoding *Bacillus subtilis* hydrolase starts around the kilobases shown in Table I counting from the point of origin in the *Bacillus subtilis* strain I-168 (Anagnostopala, 1961, J. Bacteriol., 81:741–746 or Bacillus Genomic Stock Center, accession 1A1, Columbus, Ohio). The *Bacillus subtilis* point of origin has been described in Ogasawara, N. (1995, Microbiology 141:Pt.2 257–59).

*Bacillus subtilis* hydrolase has a length of 415 amino acids. Based upon the location of the DNA encoding *Bacillus subtilis* hydrolase, naturally occurring *B. subtilis* hydrolase can be obtained by methods known to those of skill in the art including PCR technology. The nucleotide sequence for the hydrolases disclosed in Table I can be found in Nature 1997 vol 390, pages 249–256.

TABLE I

| hydrolase designation | SEQ ID NO: | kb from pt of origin |
|---|---|---|
| YUXL | SEQ ID NO: 1 | 3111 |
| YTMA | SEQ ID NO: 2 | 3131 |
| YITV | SEQ ID NO: 3 | 1190 |
| YQKD | SEQ ID NO: 4 | 2459 |
| YCLE | SEQ ID NO: 5 | 414 |
| YTAP | SEQ ID NO: 6 | 3095 |
| YDEN | SEQ ID NO: 7 | 573 |
| YDJP | SEQ ID NO: 10 | 682 |
| YVFQ | SEQ ID NO: 11 | 3496 |
| YQJL | SEQ ID NO: 13 | 2476 |
| SRFAD | SEQ ID NO: 14 | 401 |
| YCGS | SEQ ID NO: 15 | 352 |
| YTPA | SEQ ID NO: 21 | 3122 |
| YBAC | SEQ ID NO: 16 | 134 |
| YUII | SEQ ID NO: 17 | 3291 |
| YODD | SEQ ID NO: 18 | 2128 |
| YODH | SEQ ID NO: 20 | 2132 |
| YBFK | SEQ ID NO: 8 | 246 |
| YVAM | SEQ ID NO: 12 | 3452 |
| YFHM | SEQ ID NO: 9 | 929 |
| YJCH | SEQ ID NO: 19 | |

Oligonucleotide sequences or primers of about 10–30 nucleotides in length can be designed from the naturally occurring polynucleotide sequences and used in PCR technology to isolate the naturally occurring sequence from *B. subtilis* genomic sequences.

Another general strategy for the "cloning" of *B. subtilis* genomic DNA pieces for sequencing uses inverse PCR. A known region is scanned for a set of appropriate restriction enzyme cleavage sites and inverse PCR is performed with a set of DNA primers determined from the outermost DNA sequence. The DNA fragments from the inverse PCR are directly used as template in the sequencing reaction. The newly derived sequences can be used to design new oligonucleotides. These new oligonucleotides are used to amplify DNA fragments with genomic DNA as template. The sequence determination on both strands of a DNA region is finished by applying a primer walking strategy on the genomic PCR fragments. The benefit of multiple starting points in the primer walking results from the series of inverse PCR fragments with different sizes of new "cloned" DNA pieces. From the most external DNA sequence, a new round of inverse PCR is stated. The whole inverse PCR strategy is based on the sequential use of conventional taq polymerase and the use of long range inverse PCR in those cases in which the taq polymerase failed to amplify DNA fragments. Nucleic acid sequencing is performed using standard technology. One method for nucleic acid sequencing involves the use of a Perkin-Elmer Applied Biosystems 373 DNA sequencer (Perkin-Elmer, Foster City, Calif.) according to manufacturer's instructions.

Nucleic acid sequences derived from genomic DNA may contain regulatory regions in addition to coding regions. Whatever the source, the isolated hydrolase gene should be molecularly cloned into a suitable vector for propagation of the gene.

In molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the hydrolase may be accomplished in a number of ways. For example, a *B. subtilis* hydrolase gene of the present invention or its specific RNA, or a fragment thereof, such as a probe or primer, may be isolated and labeled and then used in hybridization assays to detect a gram positive hydrolase gene. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram positive hydrolase polynucleotide homologues which comprises hybridizing part or all of a nucleic acid sequence of *B. subtilis* hydrolase with gram positive microorganism nucleic acid of either genomic or cDNA origin.

Also included within the scope of the present invention is the use of gram positive microorganism polynucleotide sequences that are capable of hybridizing to the nucleotide sequence of *B. subtilis* hydrolase under conditions of intermediate to maximal stringency. Hybridization conditions are based on the melting temperature (Tm) of the nucleic acid binding complex, as taught in Berger and Kimmel (1987, *Guide to Molecular Cloning Techniques. Methods in Enzymology*, Vol. 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologues.

The term "hybridization" as used herein shall include "the process by which a strand of nucleic acid joins with a complementary strand through base pairing" (Coombs, J., (1994), *Dictionary of Biotechnology*, Stockton Press, New York, N.Y.).

The process of amplification as carried out in polymerase chain reaction (PCR) technologies is described in Dieffenbach, CW and GS Dveksler, (*PCR Primer, a Laboratory Manual*, Cold Spring Harbor Press, Plainview, N.Y., 1995). A nucleic acid sequence of at least about 10 nucleotides and as many as about 60 nucleotides from *B. subtilis* hydrolase, preferably about 12 to 30 nucleotides, and more preferably about 20–25 nucleotides can be used as a probe or PCR primer.

The *B. subtilis* hydrolase amino acid sequences shown in the Sequences were identified via a BLAST search (Altschul, Stephen, Basic local alignment search tool, *J. Mol. Biol.*, 215:403–410) of translated Bacillus subtilis genomic nucleic acid sequences. The conserved catalytic residues of the hydrolases are illustrated in Table 11.

TABLE II

| hydrolase designation | nucleophile residue | acid residue E/D | histidine residue |
|---|---|---|---|
| YUXL[1] | GSY 518 | D599 | 631 |
| YTMA[1] | FSR 122 | D204 | 236 |
| YITV[1] | TSM 116 | D201 | 237 |
| YQKD[1] | ESM 160 | D249 | 278 |
| YCLE | HSG 95 | D232 | 261 |
| YTAP | MSM 169 | D244 | 281 |
| YDEN | HSL 71 | D137 | 161 |
| YBFK | LSL 129 | E244 | 273 |
| YFHM | HDW 102 | D237 | 265 |
| YDJP | WSM 94 | D217 | 246 |
| YVFQ[2] | HSV 96 | D219 | 247 |
| YVAM[2] | YSA 93 | D207 | 233 |
| YQJL | HSY 102 | | |
| SRFAD | HSM 86 | D 190 | H 210 |
| YCGS | ISA 68 | D 207 | H 235 |
| YTPA | HSM 88 | | |
| YBAC | HSW 115 | D 266 | H 296 |
| YUII | HSL 188 | | |
| YODD | YSN 100 | | |
| YJCH | DSL 129 | | |
| YODH | RSY 172 | | |

[1]hydrolases appear to have overall amino acid similarity to one another
[2]hydrolases appear to have overall amino acid similarity to one another II. Expression Systems The present invention provides host cells, expression methods and systems for the enhanced production and secretion of gram positive microorganism hydrolases. In one embodiment of the present invention, the host cell is a gram negative host cell and in another embodiment, the host cell is a gram positive host cell. The host cell may also be a fungal or mammalian host cell. In one embodiment of the present invention, a gram positive or gram negative microorganism is genetically engineered to produce and/or over-produce a hydrolase of the present invention.

III. Production of Hydrolase

For production of hydrolase in a host cell, an expression vector comprising at least one copy of nucleic acid encoding a gram positive microorganism hydrolase, and preferably comprising multiple copies, is transformed into the host cell under conditions suitable for expression of the hydrolase. In accordance with the present invention, polynucleotides which encode a gram positive microorganism hydrolase, or fragments thereof, or fusion proteins or polynucleotide homologue sequences that encode amino acid variants of *B. subtilis* hydrolase, may be used to generate recombinant DNA molecules that direct their expression in host cells. In a preferred embodiment, the gram positive host cell belongs to the genus Bacillus. In a further preferred embodiment, the gram positive host cell is *B. subtilis*.

As will be understood by those of skill in the art, it may be advantageous to produce polynucleotide sequences possessing non-naturally occurring codons. Codons preferred by a particular gram positive host cell (Murray, E. et al., (1989), *Nuc. Acids Res..* 17:477–508) can be selected, for example, to increase the rate of expression or to produce recombinant RNA transcripts having desirable properties, such as a longer half-life, than transcripts produced from a naturally occurring sequence.

Altered hydrolase polynucleotide sequences which may be used in accordance with the invention include deletions, insertions or substitutions of different nucleotide residues resulting in a polynucleotide that encodes the same or a functionally equivalent hydrolase homologue, respectively. As used herein a "deletion" is defined as a change in the nucleotide sequence of the hydrolase resulting in the absence of one or more amino acid residues.

As used herein, an "insertion" or "addition" is that change in the nucleotide sequence which results in the addition of one or more amino acid residues as compared to the naturally occurring hydrolase.

As used herein, "substitution" results from the replacement of one or more nucleotides or amino acids by different nucleotides or amino acids, respectively. The change(s) in the nucleotides(s) can either result in a change in the amino acid sequence or not.

The encoded protein may also show deletions, insertions or substitutions of amino acid residues which produce a silent change and result in a functionally equivalent hydrolase variant. Deliberate amino acid substitutions may be made on the basis of similarity in polarity, charge, solubility, hydrophobicity, hydrophilicity, and/or the amphipathic nature of the residues as long as the variant retains its proteolytic ability. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The hydrolase polynucleotides of the present invention may be engineered in order to modify the cloning, processing and/or expression of the gene product. For example, mutations may be introduced using techniques which are well known in the art, i.e., site-directed mutagenesis to insert new restriction sites, to alter glycosylation patterns or to change codon preference, for example.

In one embodiment of the present invention, a gram positive microorganism hydrolase polynucleotide may be ligated to a heterologous sequence to encode a fusion protein. A fusion protein may also be engineered to contain a cleavage site located between the hydrolase nucleotide sequence and the heterologous protein sequence, so that the hydrolase may be cleaved and purified away from the heterologous moiety.

IV. Vector Sequences

Expression vectors used in expressing the hydrolases of the present invention in gram positive microorganisms comprise at least one promoter associated with the hydrolase, which promoter is functional in the host cell. In one embodiment of the present invention, the promoter is the wild-type promoter for the selected hydrolase and in another embodiment of the present invention, the promoter is heterologous to the hydrolase, but still functional in the host cell. In one preferred embodiment of the present invention, nucleic acid encoding the hydrolase is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term "selectable marker" refers to a gene capable of expression in the gram positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production Bacillus subtilis hydrolase or hydrolase homologues including bacterial, fungal, mammalian and insects cells. General transformation procedures are taught in *Current Protocols In Molecular Biology*, (Vol. 1, edited by Ausubel et al., John Wiley & Sons, Inc., 1987, Chapter 9) and include calcium phosphate methods, transformation using DEAE-Dextran and electroporation. Plant transformation methods are taught in Rodriquez (WO 95/14099, published May 26, 1995).

In a preferred embodiment, the host cell is a gram positive microorganism and in another preferred embodiment, the host cell is Bacillus. In one embodiment of the present invention, nucleic acid encoding one or more hydrolase(s) of the present invention is introduced into a host cell via an expression vector capable of replicating within the Bacillus host cell. Suitable replicating plasmids for Bacillus are described in *Molecular Biological Methods for Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a hydrolase(s) of the present invention is stably integrated into the microorganism genome. Preferred host cells are gram positive host cells. Another preferred host is Bacillus. Another preferred host is *Bacillus subtilis*. Several strategies have been described in the literature for the direct cloning of DNA in Bacillus. Plasmid marker rescue transformation involves the uptake of a donor plasmid by competent cells carrying a partially homologous resident plasmid (Contente et al., Plasmid, 2:555–571 (1979); Haima et al., Mol. Gen. Genet., 223:185–191 (1990); Weinrauch et al., J. Bacteriol., 154(3):1077–1087 (1983); and Weinrauch et al., J. Bacteriol.,169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979), Mol. Gen. Genet., 168:111–115; for *B. megaterium* in Vorobjeva et al., (1980), FEMS Microbiol. Letters, 7:261–263; for *B. amyloliquefaciens* in Smith et al., (1986), Appl. and Env. Microbiol., 51:634; for *B. thuringiensis* in Fisher et al., (1981), Arch. Microbiol., 139:213–217; for *B. sphaericus* in McDonald, (1984), J. Gen. Microbiol., 130:203; and *B. larvae* in Bakhiet et al., (1985, Appl. Environ. Microbiol. 49:577). Mann et al., (1986, Current Microbiol., 13:131–135) report on transformation of Bacillus protoplasts and Holubova, (1985), Folia Microbiol., 30:97) disclose methods for introducing DNA into protoplasts using DNA containing liposomes.

VI. Identification of Transformants

Whether a host cell has been transformed with a mutated or a naturally occurring gene encoding a gram positive hydrolase detection of the presence/absence of marker gene expression can suggest whether the gene of interest is present. However, its expression should be confirmed. For example, if the nucleic acid encoding a hydrolase is inserted within a marker gene sequence, recombinant cells containing the insert can be identified by the absence of marker gene function. Alternatively, a marker gene can be placed in tandem with nucleic acid encoding the hydrolase under the control of a single promoter. Expression of the marker gene in response to induction or selection usually indicates expression of the hydrolase as well.

Alternatively, host cells which contain the coding sequence for a hydrolase and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the hydrolase polynucleotide sequence can be detected by DNA-DNA or DNA-RNA hybridization or amplification using probes, portions or fragments of B. subtilis hydrolase.

VII. Assay of Activity

There are various assays known to those of skill in the art for detecting and measuring hydrolytic activity. There are assays based upon the release of acid-soluble peptides from casein or hemoglobin measured as absorbance at 280 nm or calorimetrically using the Folin method (Bergmeyer, et al., 1984, *Methods of Enzymatic Analysis*, Vol. 5, Peptidases, Proteinases and their Inhibitors, Verlag Chemie, Weinheim). Other assays involve the solubilization of chromogenic substrates (Ward, 1983, Proteinases, in *Microbial Enzymes and Biotechnology*, (W. M. Fogarty, ed.), Applied Science, London, pp. 251–317). Other assays for specific hydrolases, such as esterases, lipases, peroxidases, are known by those of skill in the art.

VIII. Secretion of Recombinant Proteins

Means for determining the levels of secretion of a heterologous or homologous protein in a gram positive host cell and detecting secreted proteins include using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton, R. et al., (1990, *Serological Methods, a Laboratory Manual*, APS Press, St. Paul Minn.) and Maddox, DE et al., (1983, *J. Exp. Med.*, 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp. (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437: 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding hydrolases may be cultured under conditions suitable for the expression and recovery of the hydrolase from cell culture. Other recombinant constructions may join the hydrolase sequences to a nucleotide sequence encoding a polypeptide domain which will facilitate purification of soluble proteins (Kroll, D J. et al., (1993), *DNA Cell Biol.*, 12:441–53).

Such purification facilitating domains include, but are not limited to, metal chelating peptides such as histidine-tryptophan modules that allow purification on immobilized metals (Porath, J., (1992), *Protein Expr. Purif.* 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of The Present Invention

Hydrolase and Genetically Engineered Host Cells

The present invention provides genetically engineered host cells comprising nucleic acid encoding hydrolases of the present invention. The host cell may contain other modifications, e.g., protease deletions, such as deletions of the mature subtilisn protease and/or mature neutral protease disclosed in U.S. Pat. No. 5,264,366 or other modifications to enhance expression.

In a preferred embodiment, the host cell is a Bacillus. In a further preferred embodiment, the host cell is a *Bacillus subtilis*.

In a preferred embodiment, the host cell is grown under large scale fermentation conditions. In another preferred embodiment, the hydrolase is isolated and/or purified and used in the textile industry, the feed industry and in cleaning compositions such as detergents.

As noted, hydrolase can be useful in formulating various cleaning compositions. A number of known compounds are suitable surfactants useful in compositions comprising the hydrolase of the invention. These include nonionic, anionic, cationic, anionic or zwitterionic detergents, as disclosed in U.S. Pat. No. 4,404,128 and U.S. Pat. No. 4,261,868. A suitable detergent formulation is that described in Example 7 of U.S. Pat. No. 5,204,015. The art is familiar with the different formulations which can be used as cleaning compositions. In addition, hydrolase can be used, for example, in bar or liquid soap applications, dishcare formulations, contact lens cleaning solutions or products, peptide hydrolysis, waste treatment, textile applications, as fusion-cleavage enzymes in protein production, etc. hydrolase may comprise enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

Hydrolases of the present invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of hydrolase to conventional cleaning compositions does not create any special use limitation. In other words, any temperature and pH suitable for the detergent is also suitable for the present compositions as long as the pH is within the above range, and the temperature is below the described hydrolase denaturing temperature. In addition, hydrolase can be used in a cleaning composition without detergents, again either alone or in combination with builders and stabilizers.

Hydrolases can be included in animal feed such as part of animal feed additives as described in, for example, U.S. Pat. Nos. 5,612,055; 5,314,692; and 5,147,642.

One aspect of the invention is a composition for the treatment of a textile that comprises a hydrolase. The composition can be used to treat for example silk or wool as described in publications such as RD 216,034; EP 134,267; U.S. Pat. No. 4,533,359; and EP 344,259.

Hydrolase Polynucleotides

A *B. subtlis* hydrolase polynucleotide, or any part thereof, provides the basis for detecting the presence of gram positive microorganism hydrolase polynucleotide homologues through hybridization techniques and PCR technology.

Accordingly, one aspect of the present invention is to provide for nucleic acid hybridization and PCR probes which can be used to detect polynucleotide sequences, including genomic and cDNA sequences, encoding gram positive hydrolase or portions thereof.

The manner and method of carrying out the present invention may be more fully understood by those of skill in the art by reference to the following examples, which examples are not intended in any manner to limit the scope of the present invention or of the claims directed thereto.

EXAMPLE I

Preparation of a Genomic library

The following example illustrates the preparation of a Bacillus genomic library.

Genomic DNA from Bacillus cells is prepared as taught in *Current Protocols In Molecular Biology*, Vol. 1, edited by Ausubel et al., John Wiley & Sons, Inc.,1987, Chapter 2. 4.1. Generally, Bacillus cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the Bacillus genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested Bacillus genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram Positive Microorganism Hydrolase

The following example describes the detection of gram positive microorganism hydrolase DNA derived from a gram positive microorganism is prepared according to the methods disclosed in *Current Protocols in Molecular Biology*, Chap. 2 or 3. The nucleic acid is subjected to hybridization and/or PCR amplification with a probe or primer derived from hydrolase The nucleic acid probe is labeled by combining 50 pmol of the nucleic acid and 250 mCi of [gamma $^{32}$P] adenosine triphosphate (Amersham, Chicago Ill.) and T4 polynucleotide kinase ((DuPont NE®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologues of *B. subtilis* hydrolase. The homologues are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

What is claimed is:

1. An isolated nucleic acid encoding a protein which hydrolyzes a peptide bond comprising an amino acid sequence selected from the group consisting of SEQ ID NO: 2 (YTMA), SEQ ID NO: 8 (YBFK), SEQ ID NO: 9 (YFHM), SEQ ID NO: 10 (YDJP), SEQ ID NO: 12 (YVAM), SEQ ID NO: 17 (YUII), SEQ ID NO: 18 (YODD), SEQ ID NO: 19 (YJCH), SEQ ID NO: 20 (YODH), SEQ ID NO: 21 (YTPA) and a naturally occurring amino acid sequence having at least 90% sequence identity to SEQ ID NOs: 2, 8, 9, 10, 12, 17, 18, 19, 20, or 21.

2. The isolated nucleic acid of claim 1, wherein said nucleic acid encodes said protein comprising an amino acid sequence selected from the group consisting of SEQ ID NO: 2 (YTMA), SEQ ID NO: 8 (YBFK), SEQ ID NO: 9 (YFHM), SEQ ID NO: 10 (YDJP), SEQ ID NO: 12 (YVAM), SEQ ID NO: 17 (YUII), SEQ ID NO: 18 (YODD), SEQ ID NO: 19 (YJCH), SEQ ID NO: 20 (YODH), and SEQ ID NO: 21 (YTPA).

3. The isolated nucleic acid of claim 1, wherein said nucleic acid encodes said protein comprising a naturally occurring amino acid sequence having 95% sequence identity to SEQ ID NOs: 2, 8, 9, 10, 12, 17, 18, 19, 20, or 21.

4. A vector comprising the nucleic acid of claim 1.

5. A host cell comprising the nucleic acid of claim 1.

6. A host cell comprising the vector of claim 4.

7. The host cell of claim 5 or 6, wherein said host cell is a microorganism from the genus Bacillus.

8. The microorganism according to claim 7, wherein said microorganism is selected from the group consisting of *B. subtilis, B. licheniformis, B. lentus, M. brevis, B. stearothermophilus, B. alkalophilus, B. amyloliquifaciens, B. coagulans, B. circulans, B. lautus* and *B. thuringiensis*.

9. An isolated protein which hydrolyzes a peptide bond comprising an amino acid sequence selected from the group consisting of SEQ ID NO: 2 (YTMA), SEQ ID NO: 8 (YBFK), SEQ ID NO: 9 (YFHM), SEQ ID NO: 10 (YDJP), SEQ ID NO: 12 (YVAM), SEQ ID NO: 17 (YUII), SEQ ID NO: 18 (YODD), SEQ ID NO: 19 (YJCH), SEQ ID NO: 20 (YODH), SEQ ID NO: 21 (YTPA) and a naturally occurring amino acid sequence having at least 90% sequence identity to SEQ ID NOs: 2, 8, 9, 10, 12, 17, 18, 19, 20, or 21.

10. The isolated protein of claim 9, wherein said amino acid sequence is SEQ ID NO: 2 (YTMA), SEQ ID NO: 8 (YBFK), SEQ ID NO: 9 (YFHM), SEQ ID NO: 10 (YDJP), SEQ ID NO: 12 (YVAM), SEQ ID NO: 17 (YUII), SEQ ID NO: 18 (YODD), SEQ ID NO: 19 (YJCH), SEQ ID NO: 20 (YODH), or SEQ ID NO: 21 (YTPA).

11. The isolated protein of claim 9, wherein said protein has a naturally occurring amino acid sequence having at least 95% sequence identity to SEQ ID NOs.; 9 2, 8, 9, 10, 12, 17, 18, 19, 20, or 21.

12. A cleaning solution comprising the protein of claim 9.

13. An animal feed comprising the protein of claim 9.

14. A composition for the treatment of textiles comprising the protein of claim 9.

15. A method for treating a textile comprising;
a) obtaining a composition comprising a protein which hydrolyzes a peptide bond having an amino acid sequence selected from the group consisting of SEQ ID NO: 1 (YUXL), SEQ ID NO: 2 (YTMA), SEQ ID NO: 3 (YITV), SEQ ID NO: 4 (YQKD), SEQ ID NO: 5 (YCLE), SEQ I: NO: 6 (YTAP), SEQ ID NO: 7 (YDEN), SEQ ID NO: 8 (YBFK), SEQ ID NO: 9 (YFHM), SEQ ID NO: 10 (YDJP), SEQ ID NO: 11 (YVFQ), SEQ ID NO: 12 (YVAM), SEQ ID NO: 13 (YQJL), SEQ ID NO: 14 (SRFAD), SEQ ID NO: 15 (YCGS), SEQ ID NO: 16 (YBAC), SEQ ID NO: 17 (YUII), SEQ ID NO: 18 (YODD), SEQ ID NO: 19 (YJCH), SEQ ID NO: 20 (YODH), SEQ ID NO: 21 (YTPA) and an amino acid sequence having 90% identity to a sequence of SEQ ID NOs: 1–21; and
b) treating the textile with said composition.

16. The method according to claim 15, wherein the amino acid sequence of the protein is SEQ ID NO: 1 (YUXL), SEQ ID NO: 3 (YITV), SEQ ID NO: 4 (YQKD), SEQ ID NO: 5 (YCLE), SEQ ID NO: 6 (YTAP), SEQ ID NO: 7 (YDEN), SEQ ID NO: 11 (YVFQ), SEQ ID NO: 13 (YQJL), SEQ ID NO: 14 (SRFAD), SEQ ID NO: 15 (YCGS) or an amino acid sequence having 95% identity thereto.

17. A method for formulating a cleaning composition comprising,
a) obtaining a protein which hydrolyzes a peptide bond comprising an amino acid sequence selected from the group consisting of SEQ ID NO: 1 (YUXL), SEQ ID NO: 2 (YTMA), SEQ ID NO: 3 (YITV), SEQ ID NO: 4 (YQKD), SEQ ID NO: 5 (YCLE), SEQ ID NO: 6 (YTAP), SEQ ID NO: 7 (YDEN), SEQ ID NO: 8 (YBFK), SEQ ID NO: 9 (YFHM), SEQ ID NO: 10 (YDJP), SEQ ID NO: 11 (YVFQ), SEQ ID NO: 12 (YVAM), SEQ ID NO: 13 (YQJL), SEQ ID NO: 14 (SRFAD), SEQ ID NO: 15 (YCGS), SEQ ID NO: 16

(YBAC), SEQ ID NO: 17 (YUII), SEQ ID NO: 18 (YODD), SEQ ID NO: 19 (YJCH), SEQ ID NO: 20 (YODH), SEQ ID NO: 21 (YTPA) and an amino acid sequence having 90% identity to a sequence of SEQ ID NOs.: 1–21; and b) combining said protein with a surfactant to produce the cleaning composition.

18. The method according to claim 17, wherein the cleaning composition is a detergent composition.

19. The method according to claim 17, wherein the amino acid sequence of the protein is SEQ ID NO: 1 (YUXL), SEQ ID NO: 3 (YITV), SEQ ID NO: 4 (YQKD), SEQ ID NO: 5 (YCLE), SEQ ID NO: 6 (YTAP), SEQ ID NO: 7 (YDEN), SEQ ID NO: 11 (YVFQ), SEQ ID NO: 13 (YQJL), SEQ ID NO: 14 (SRFAD), SEQ ID NO: 15 (YCGS) or a naturally occurring amino acid sequence having at least 95% amino acid sequence identity thereto.

20. A method for formulating an animal feed comprising, a) obtaining a protein which hydrolyzes a peptide bond comprising an amino acid sequence selected from the group consisting of SEQ ID NO: 1 YUXL), SEQ ID NO: 2 (YTMA), SEQ ID NO. 3 (YITV), SEQ ID NO: 4 (YQKD), SEQ ID NO: 5 (YCLE), SEQ ID NO: 6 (YTAP), SEQ ID NO: 7 (YDEN), SEQ ID NO: 8 (YBFK), SEQ ID NO: 9 (YFHM), SEQ ID NO: 10 (YDJP), SEQ ID NO: 11 (YVFQ), SEQ ID NO: 12 (YVAM), SEQ ID NO: 13 (YQJL), SEQ ID NO: 14 (SRFAD), SEQ ID NO: 15 (YCGS), SEQ ID NO: 16 (YBAC), SEQ ID NO: 17 (YUII), SEQ ID NO: 18 (YODD), SEQ ID NO: 19 (YJCH), SEQ ID NO: 20 (YODH), SEQ ID NO: 21 (YTPA), wherein said protein is used as an additive in an animal feed; and b) combining said protein with the animal feed.

21. The method according to claim 20, wherein the amino acid sequence of the protein is a naturally occurring amino acid sequence having at least 95% identity to any one sequence of SEQ ID NOs: 1–21.

* * * * *

UNITED STATES PATENT AND TRADEMARK OFFICE
CERTIFICATE OF CORRECTION

PATENT NO.    : 6,316,241 B1
DATED         : November 13, 2001
INVENTOR(S)   : David A. Estell It is certified that error appears in the above-identified patent and that said Letters Patent is hereby corrected as shown below:

Column 46,
Lines 26 - 27, after "indentity to" text should read:   -- SEQ ID Nos.:  2, 8, 9 10, 12, 17, 18, 19, 20 or 21. --

Signed and Sealed this

Twentieth Day of May, 2003

JAMES E. ROGAN
*Director of the United States Patent and Trademark Office*